United States Patent [19]

Knieps et al.

[11] Patent Number: 5,144,033
[45] Date of Patent: Sep. 1, 1992

[54] PROCESS FOR OBTAINING ALMOST FLUORESCENCE-FREE XANTHINES

[75] Inventors: Rudolf Knieps; Ottmar Jaenicke, both of Kelkheim; Walter Schönfeld, Wiesbaden, all of Fed. Rep. of Germany

[73] Assignee: Hoechst Aktiengesellschaft, Frankfurt am Main, Fed. Rep. of Germany

[21] Appl. No.: 654,487

[22] Filed: Feb. 13, 1991

[30] Foreign Application Priority Data

Feb. 15, 1990 [DE] Fed. Rep. of Germany ....... 4004618

[51] Int. Cl.$^5$ ............................................. C07D 473/04
[52] U.S. Cl. ..................................... 544/273; 544/267
[58] Field of Search ....................... 544/267, 266, 273

[56] References Cited

FOREIGN PATENT DOCUMENTS

P21220 4/1959 German Democratic Rep. .

OTHER PUBLICATIONS

Ullmanns, Encyklopadie der technischen Chemie, "Polyacryl-Verbindungen bis Quecksilber" pp. 578-579 (1980).

*Primary Examiner*—Nicholas S. Rizzo
*Attorney, Agent, or Firm*—Finnegan, Henderson, Farabow, Garrett and Dunner

[57] ABSTRACT

Process for obtaining almost fluorescence-free xanthines by precipitation of xanthines which still contain an unsubstituted nitrogen atom in the molecule from aqueous-alkaline solution by means of $CO_2$.

6 Claims, No Drawings

PROCESS FOR OBTAINING ALMOST FLUORESCENCE-FREE XANTHINES

DESCRIPTION

The xanthine "basic structure" is the compound of the formula

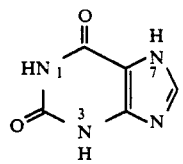

Unsubstituted xanthine and substituted xanthines are principally precursors or intermediates for the preparation of pharmaceuticals; various substituted xanthines are themselves also already used for valuable pharmaceutical active compounds. A known pharmaceutical active compound of this type, is, for example, the compound pentoxifylline (=1-(5-oxohexyl)-3,7-dimethylxanthine) which is the active principle of various pharmaceuticals for circulatory disorders. A pentoxifylline-containing pharmaceutical for the treatment of circulatory disorders is, for example, the product ®Trental marketed by the company Albert-Roussel Pharma GmbH, Wiesbaden (Federal Republic of Germany).

A preferred synthesis of the xanthine ring system is the so-called "modified Traube synthesis" (Ullmann's Enzyklopädie der Technischen Chemie [Ullmann's Encylopedia of Industrial Chemistry], 4th edition, volume 19 (1980) p. 579). The synthesis starts from urea or urea derivatives and cyanoacetic acid; it is represented, for example, for the preparation of 3-methylxanthine as follows (diagrammatically):

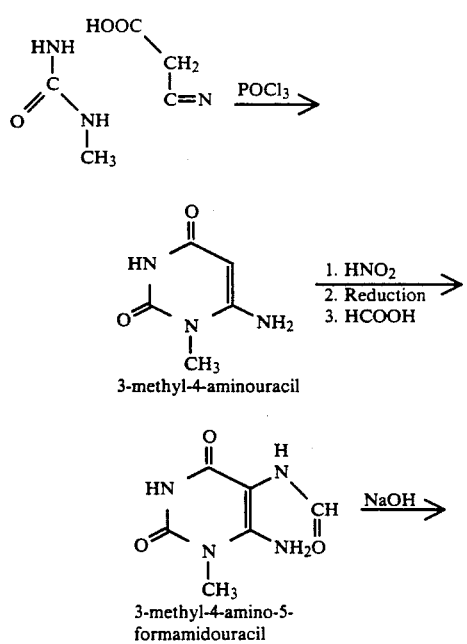

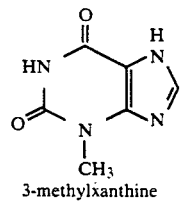

3-methylxanthine

In this synthesis—presumably in its last step (the alkaline ring closure reaction)—strongly fluorescent by-products are in some cases formed, which adhere obstinately to the xanthines after their precipitation from their alkaline solution and can only be removed by repeated reprecipitation or recrystallization accompanied by corresponding yield losses; the precipitation of the xanthines from their alkaline solution is customarily carried out by means of inorganic or organic acids such as, for example, sulfuric acid, hydrochloric acid or acetic acid.

It has already been attempted to reduce the contamination by the fluorescent by-products by adding formaldehyde during the alkaline ring closure reaction (DD-A 21,220). However, even in this process recrystallization at least once is still necessary (cf. column 2, lines 17/18 of the DD-A).

In attempting, by the abovementioned alkaline ring closure reaction, to arrive immediately—i.e. without other purification operations—at a virtually fluorescence-free xanthine or to free an already present fluorescent xanthine from the fluorescent impurities with as low an outlay as possible and with substance losses which are as low as possible, it has now surprisingly been found that this aim can be achieved by making xanthines which still contain at least one unsubstituted nitrogen atom in the molecule precipitate from aqueous-alkaline solution by means of $CO_2$ (carbon dioxide).

The precipitation by means of $CO_2$ can be carried out directly following the alkaline ring closure reaction of the corresponding diaminouracil derivatives to give the xanthine ring structure. If a fluorescent xanthine already obtained elsewhere is present, this can also be dissolved in an aqueous-alkaline solution and precipitated therefrom again by means of $CO_2$. The xanthines precipitated from the aqueous-alkaline solution by means of $CO_2$ are free or virtually free of fluorescent by-products.

The effect of the precipitation process according to the invention is possibly achieved in that the precipitation by means of $CO_2$ is carried out in a milder and more controlled manner than with the inorganic and organic acids previously used for this purpose. As a result, more uniform and ordered crystals could be formed which do not include any—or in any case hardly any—impurities.

Apart from the advantages in relation to product quality and the avoidance of yield losses, the precipitation process according to the invention also still has an ecological advantage, as the mother liquors contain ecologically harmless carbonate instead of sulfates, chlorides or acetates and the use of solvents for dehydration of the filtered or centrifuged xanthine products can also be dispensed with owing to the substantially improved crystallinity.

All xanthines still containing at least one unsubstituted nitrogen atom in the molecule are in principle open to the process according to the invention; i.e. weakly acidic compounds which dissolve in aqueous-alkaline medium (NH$_4$OH, LiOH, NaOH, KOH etc.) with corresponding salt formation, owing to the acidic hydrogen on the nitrogen. The pH of the aqueous-alkaline medium is in general at least about 10.

Preferred xanthines having at least still one unsubstituted nitrogen atom in the molecule are those of the following formula I

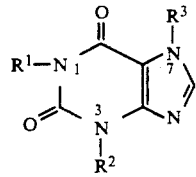

in which R$^1$, R$^2$ and R$^3$ independently of one another are H or (C$_1$–C$_6$)-alkyl, preferably H or CH$_3$, where, however, at least one of the 3 radicals must be H.

Particularly preferred xanthines for the process are 3-methylxanthine (=compound of the formula I where R$^1$=R$^3$=H and R$^2$=CH$_3$),
1,3-dimethylxanthine (=compound of the formula I where R$^1$=R$^2$=CH$_3$ and R$^3$=H; theophylline) and
3,7-dimethylxanthine (=compound of the formula I where R$^1$=H and R$^2$=R$^3$=CH$_3$; theobromine).

Virtually as much xanthine as up to the saturation limit can be dissolved in the aqueous-alkaline medium. This solution is then brought into contact with CO$_2$ to precipitate the xanthine. This can be carried out advantageously by passing CO$_2$ into the gas space of a stirring vessel partially filled with the aqueous-alkaline xanthine solution with intensive stirring of the solution. The use of an aerating stirrer or recirculation of the solution or suspension is also favorable, an intensive exchange in the style of a water jet pump taking place between the liquid and the gas carried along.

The supply of the CO$_2$ gas via a quantity control is furthermore also advantageous in order to control the crystal growth rate optimally by a controlled CO$_2$ absorption.

The final pH necessary for complete precipitation is advantageously set by means of a pressure control and controlled using a pH electrode. The said final pH is without exception still in the alkaline range (between about 7 and 9.5) and varies slightly within this range depending on the particular xanthine. The final pH necessary for complete precipitation is, for example, between about 7.5 and 8.5 for 3-methylxanthine and between about 8.8 and 9.2 for 1,3-dimethylxanthine (=theophylline) and 3,7-dimethylxanthine (=theobromine). The respective pH values can easily be determined by simple routine tests. The adjustment of the final pH can advantageously be carried out by means of the CO$_2$ pressure. A CO$_2$ excess pressure of about 0.5 to 6.0 bar is in general advantageous.

To achieve optimum crystal formation, it is also advantageous to carry out the precipitation at elevated temperature, a temperature range of about 80° C. to 110° C., in particular of about 90° C. to 100° C., being preferred.

After precipitation is complete, the product is separated from the liquid phase (for example by means of a suction filter or centrifuge) and subsequently washed with water. The product is then virtually fluorescence-free.

The precipitation process according to the invention will now be illustrated in more detail by the following examples.

EXAMPLE 1

500 g of crude 3,7-dimethylxanthine having a purity of about 97% are suspended in 3000 ml of water and dissolved at 100° C. using 114 g of sodium hydroxide solution. About 130 g of carbon dioxide are passed into the solution with vigorous stirring at a pressure of 1.0 to 1.5 bar within the course of 2–4 hours. After completion of the precipitation, the pH of the suspension is adjusted to a value of 8.8 to 9.2 by means of the CO$_2$ pressure. The suspension is cooled to 40° C. and the precipitated 3,7-dimethylxanthine is separated on a suction filter.

Yield: 95% of theory, purity: 99.9%.

EXAMPLE 2

650 kg of crude 3-methylxanthine as the sodium salt dissolved in 4200 kg of water are heated to 100° C. and about 310 kg of carbon dioxide are passed into the vessel in the course of 4 hours. The vessel contents are circulated by means of a pump during the precipitation and in this way mixed intensively with the carbon dioxide in the gas space of the stirring vessel. The CO$_2$ excess pressure in the vessel is slowly increased from 0 to 4 bar in the course of 2 hours, controlled by means of the quantity of CO$_2$. After cooling to 45° C., the 3-methylxanthine is separated in a centrifuge.

Yield: 610 kg of 3-methylxanthine corresponding to 94% of theory. The fluorescence is lower by a factor of 100 than with 3-methylxanthine which has been precipitated under comparable conditions using sulfuric acid.

We claim:

1. A process for obtaining almost fluorescence-free xanthines, which comprises precipitating xanthines which contain at least one unsubstituted nitrogen atom in the molecule from an aqueous-alkaline solution by CO$_2$.

2. The process as claimed in claim 1, wherein xanthines of the following formula I:

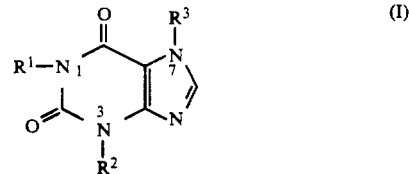

in which R$^1$, R$^2$ and R$^3$ independently of one another are H or (C$_1$–C$_6$)-alkyl, preferably H or CH$_3$, where, however, at least one of the 3 radicals must be H, are employed as xanthines which still contain at least one unsubstituted nitrogen atom in the molecule.

3. The process as claimed in claim 1, wherein
3-methylxanthine,
1,3-dimethylxanthine or
3,7-dimethylxanthine is made to precipitate.

4. The process as claimed in claim 1,
wherein a final pH of between about 7 and 9.5 is set for the precipitation.

5. The process as claimed in claim 1,
wherein the precipitation is carried out at CO$_2$ excess pressures between about 0.5 and 6 bar.

6. The process as claimed in claim 1,
wherein the precipitation is carried out at temperatures between about 80° C. and 110° C., preferably between about 90° C. and 100° C.

* * * * *